DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED AUGUST 31, 1971

889 O.G. 1362

T889,002

STABILIZATION OF 1,1,1-TRICHLOROETHANE

Milton J. Blankenship, Alte Landstrasse 64, Oberrieden, Switzerland, and Ralph McCarthy, 1865 Bush St., San Francisco, Calif. 94109

Filed Dec. 15, 1969, Ser. No. 885,339

Int. Cl. C07c *17/42*

U.S. Cl. 260—652.5R

No Drawing. 6 Pages Specification

The reaction of 1,1,1-trichloroethane with aluminum is inhibited by the presence in the 1,1,1-trichloroethane of a small amount of a dissolved amino compound of the formula $$\begin{array}{c} R-N-R' \\ | \\ R'' \end{array}$$

wherein R is a morpholinoalkyl radical, an alkylated morpholinoalkyl radical, a phenylthiomethyl radical, an alkylphenylthiomethyl radical, an aminoalkyl radical, an N-alkylated aminoalkyl radical, a polyglycol residue, a polyglycolamine residue, a halopyridinecarbonyl radical, an aminoalkylcyclohexanealkyl radical, or a dialkyl phosphono radical, R′ is hydrogen, an alkyl radical, an aminoalkyl radical, a polyalkylenepolyamine residue, an alkanoyl radical, or a polyglycol residue, and R″ is hydrogen, an alkyl radical, or a polyglycol residue. Concentrations of the order of 0.1–10 weight percent of solvent composition provide significant inhibition of the aluminum reaction.